(12) United States Patent
Kim

(10) Patent No.: US 9,956,259 B2
(45) Date of Patent: May 1, 2018

(54) PHARMACEUTICAL COMPOSITION FOR PREVENTING AND TREATING OBESITY, CONTAINING GREEN-TEA SEE HUSK EXTRACT AS ACTIVE INGREDIENT

(71) Applicant: INDUSTRY FOUNDATION OF CHONNAM NATIONAL UNIVERSITY, Gwangju (KR)

(72) Inventor: Jong Deog Kim, Jeollanam-do (KR)

(73) Assignee: INDUSTRY FOUNDATION OF CHONNAM NATIONAL UNIVERSITY (KR)

(*) Notice: Subject to any disclaimer, the term of this patent is extended or adjusted under 35 U.S.C. 154(b) by 36 days.

(21) Appl. No.: 15/018,004

(22) Filed: Feb. 8, 2016

(65) Prior Publication Data

US 2016/0151439 A1    Jun. 2, 2016

Related U.S. Application Data

(63) Continuation of application No. PCT/KR2014/007401, filed on Aug. 8, 2014.

(30) Foreign Application Priority Data

Aug. 9, 2013 (KR) .......................... 10-2013-0094999

(51) Int. Cl.
*A61K 36/82*    (2006.01)

(52) U.S. Cl.
CPC ........ *A61K 36/82* (2013.01); *A61K 2236/331* (2013.01); *A61K 2236/333* (2013.01)

(58) Field of Classification Search
CPC ........................................ A61K 36/82
USPC ........................................ 424/729
See application file for complete search history.

(56) References Cited

FOREIGN PATENT DOCUMENTS

| KR | 10-2008-0090805 | | 10/2008 | | |
|---|---|---|---|---|---|
| KR | 10-2008-0091053 | | 10/2008 | | |
| KR | 10-2010-0124519 | A | 11/2010 | | |
| KR | 10-2011-0112916 | A | 10/2011 | | |
| KR | 20130078387 | A | * 7/2013 | ............. | A61K 36/82 |

OTHER PUBLICATIONS

International Search Report prepared by the Korean Intellectual Property Office dated Nov. 5, 2014, for International Application No. PCT/KR2014/007401.
Choi, Seon Gyeong, "Antiobesity Effect of Green Tea Seed Oil", Wonkwang University Master's Degree Thesis, Feb. 2008.
Kim et al. "The Differences in Efficacy and Effect of Herbal Extracts by the Part and Solvent Extraction from the Medical Plants," J. Soc. Cosmet. Scientists Korea, Jun. 2006, vol. 32, No. 2, pp. 105-110 (English abstract and tables).

* cited by examiner

*Primary Examiner* — Christopher R Tate
*Assistant Examiner* — Deborah A Davis
(74) *Attorney, Agent, or Firm* — Sheridan Ross P.C.

(57) ABSTRACT

The present invention relates to a pharmaceutical composition for preventing and treating obesity which comprises the green tea (*Camellia sinensis* L.) seed husk extract or the fraction thereof as an active ingredient. The green tea seed husk extract exhibits a significant vasculogenesis suppressing effect and has been confirmed to be effective in reducing adipocytes and body weight, and thus the green tea seed husk extract can advantageously be used as an active ingredient in a composition for preventing and treating obesity, a health food for preventing and alleviating obesity, or a pharmaceutical composition for vasculogenesis suppression.

3 Claims, 17 Drawing Sheets

[Fig. 1]
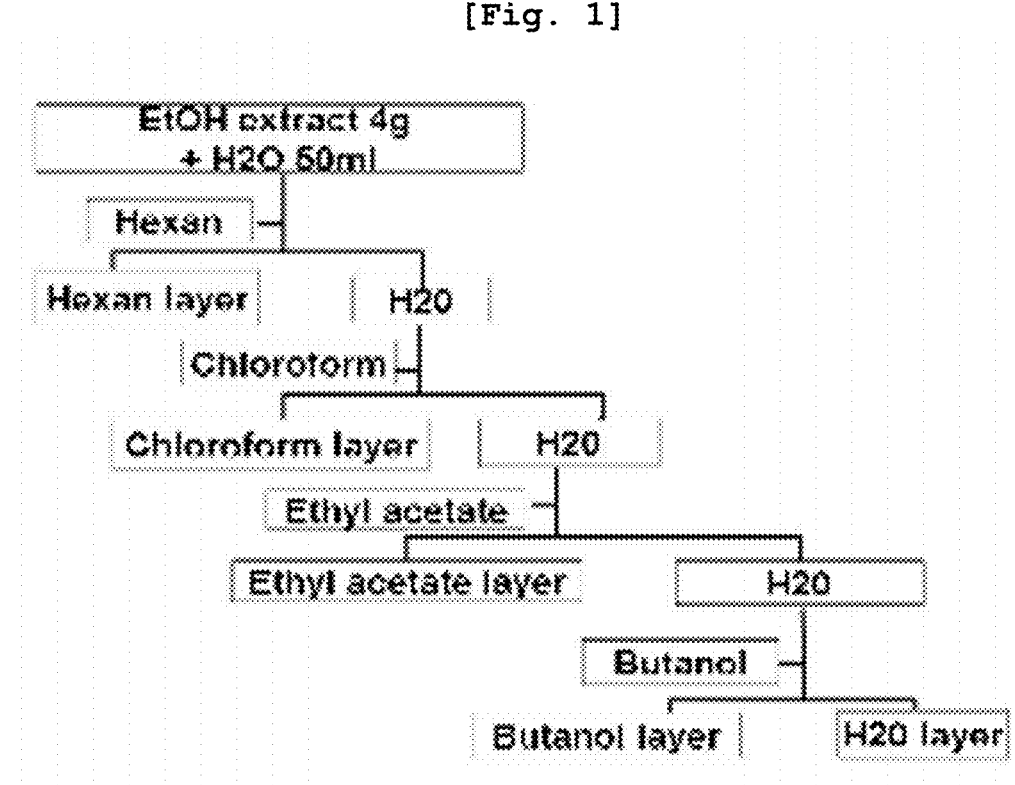

[Fig. 2]
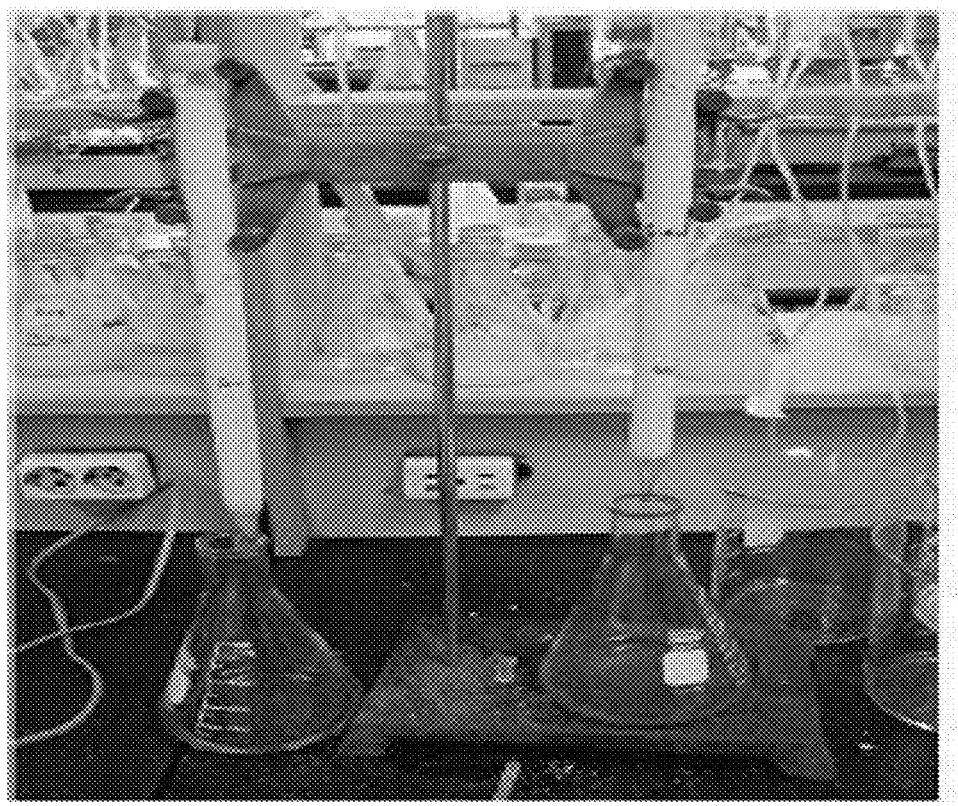

[Fig. 3]

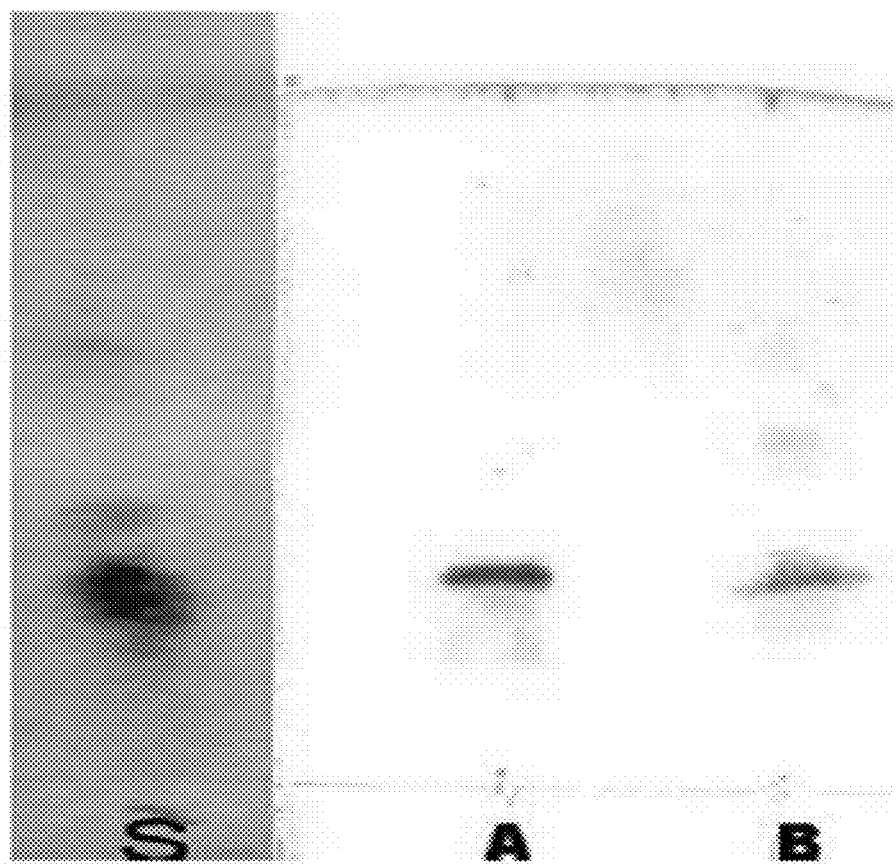
[Fig. 4]

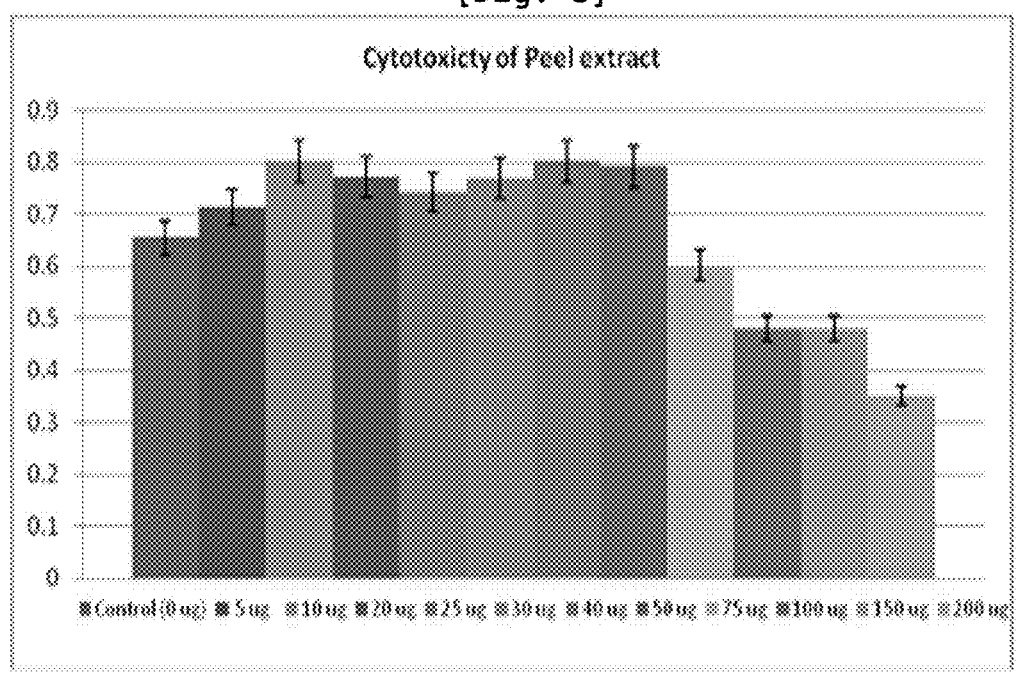

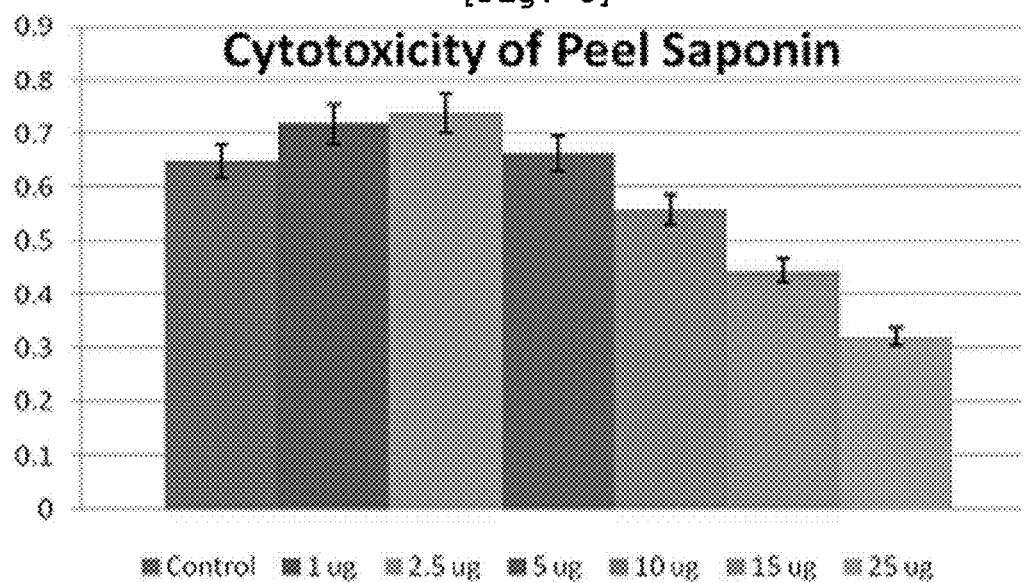

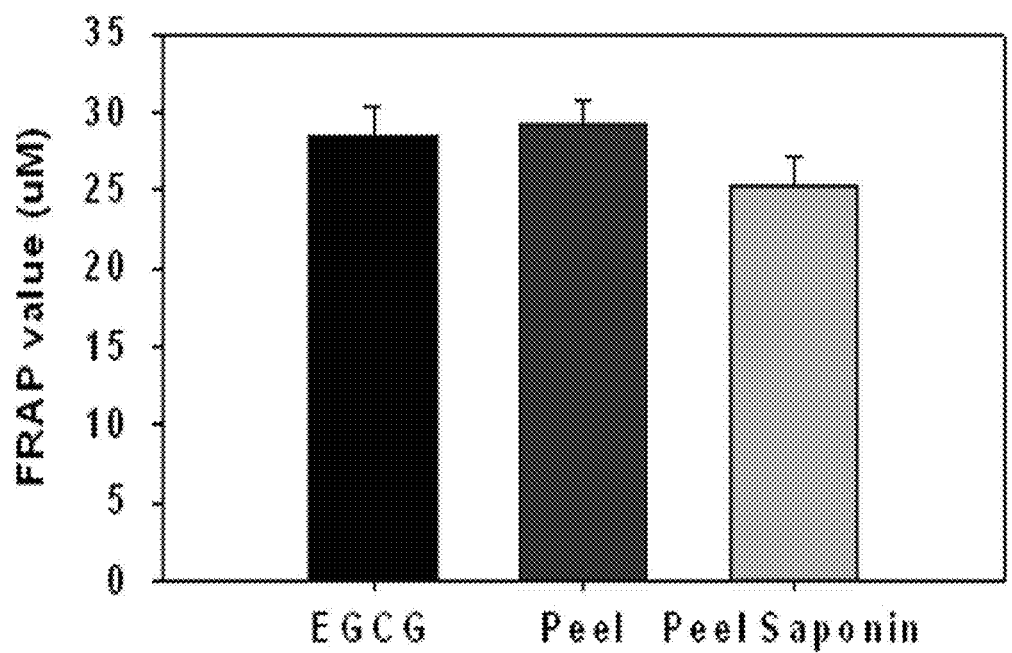

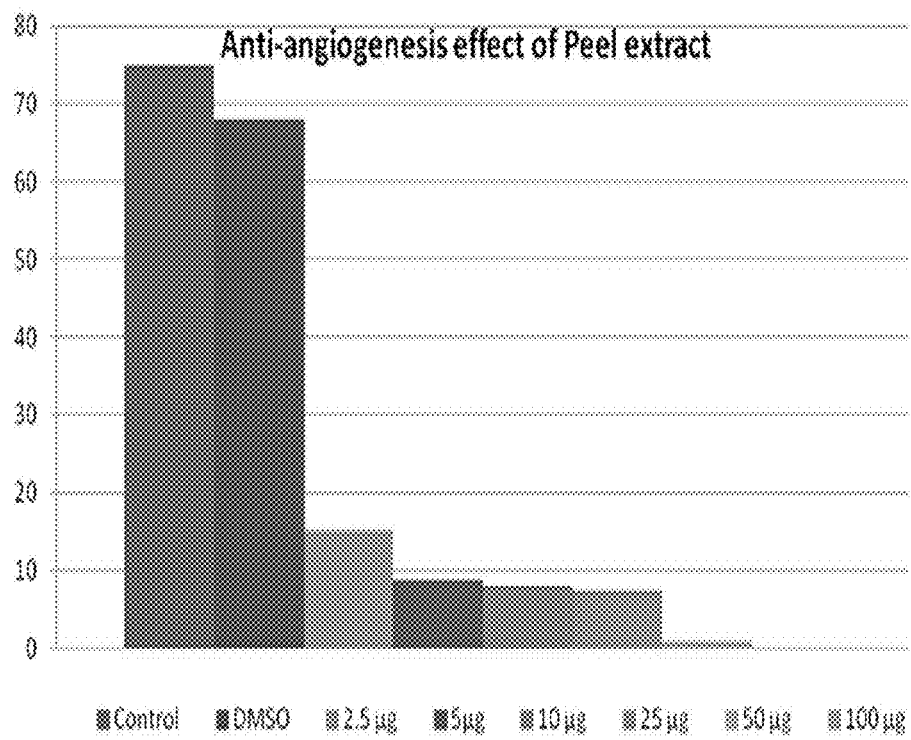

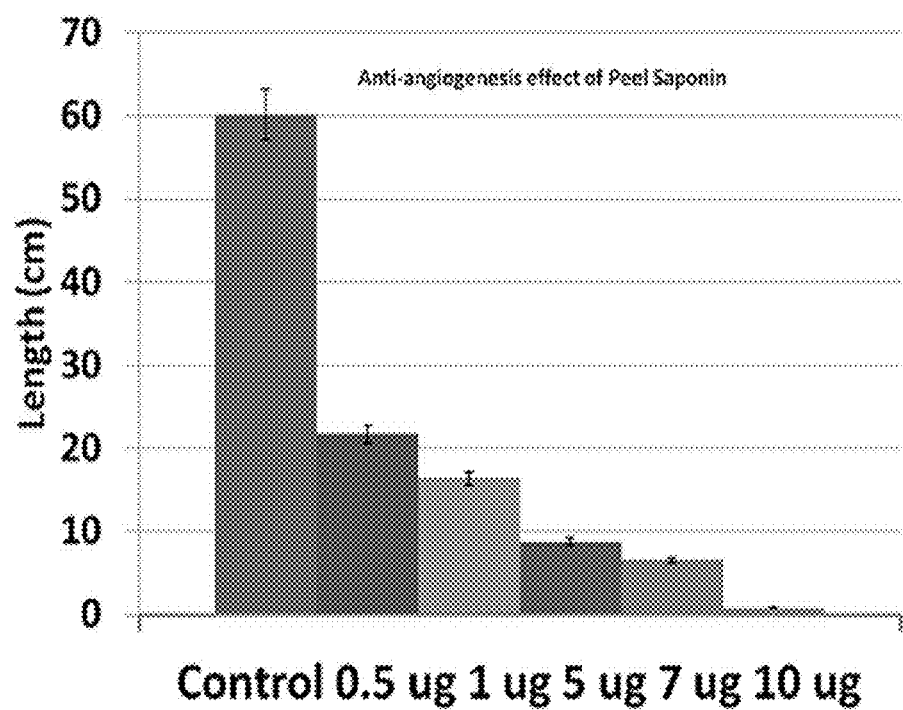
[Fig. 9]

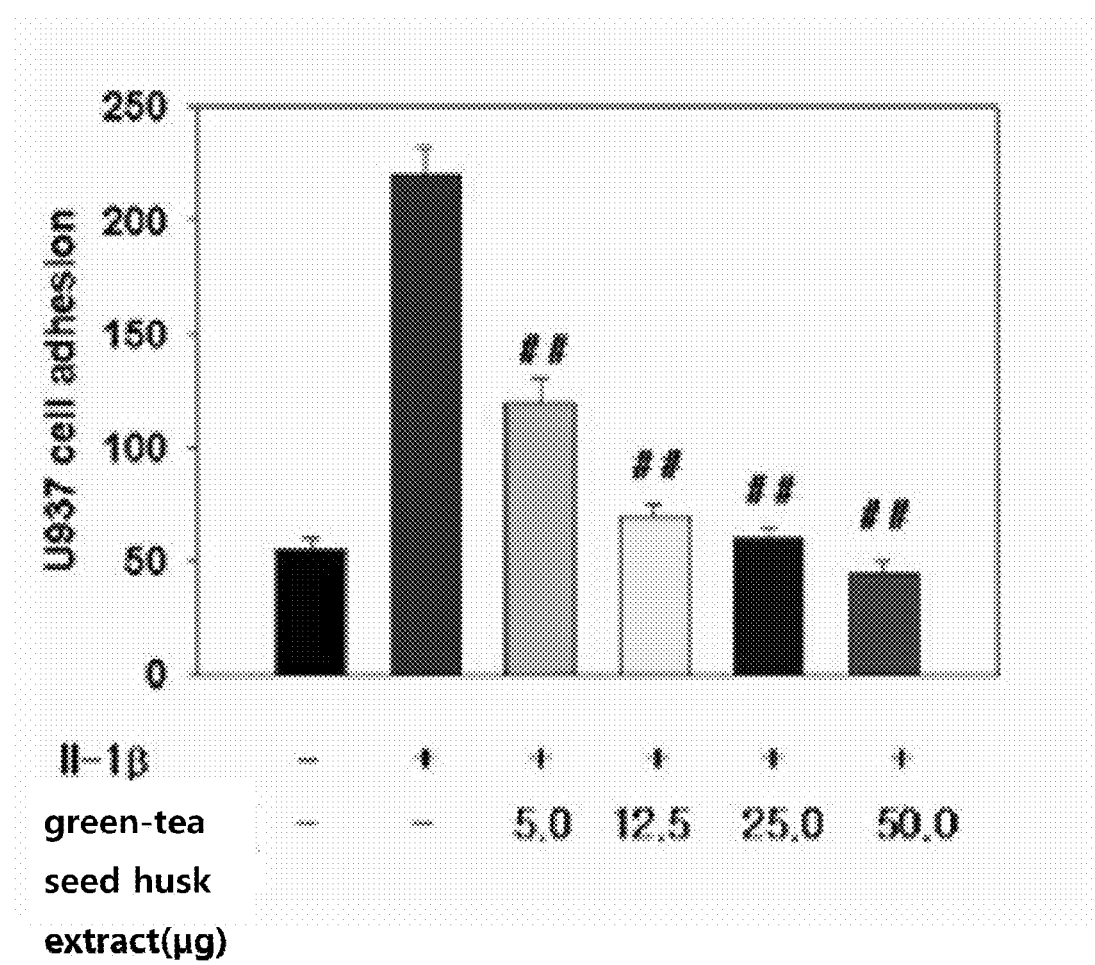
[Fig. 10]

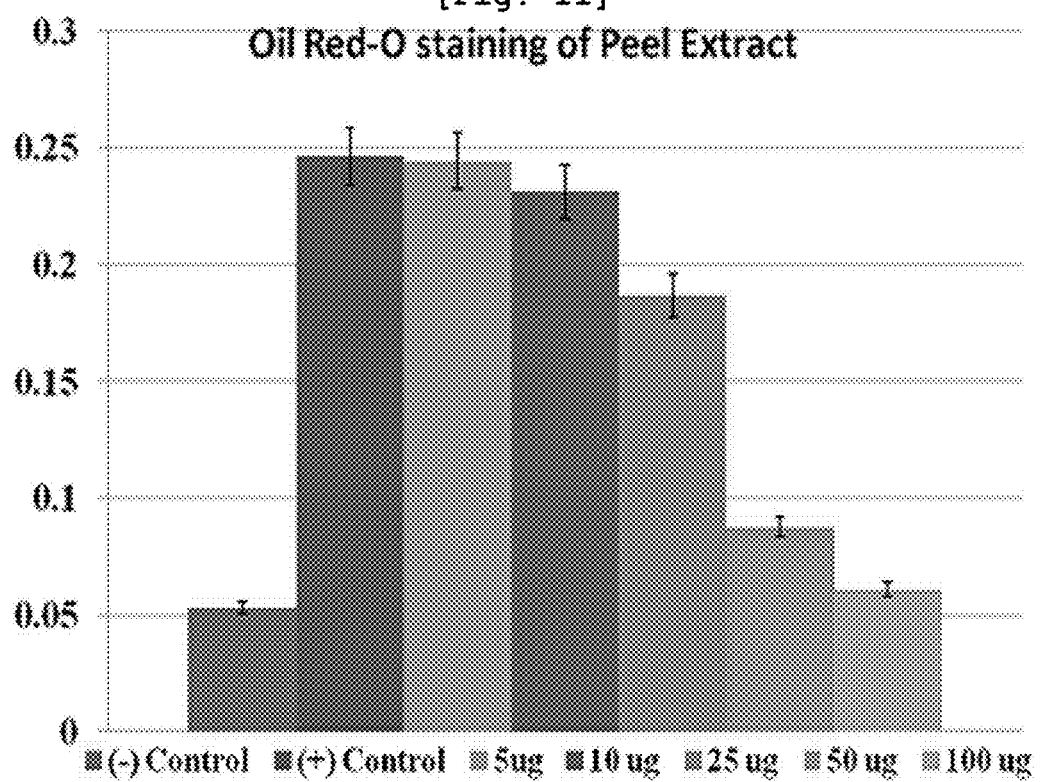

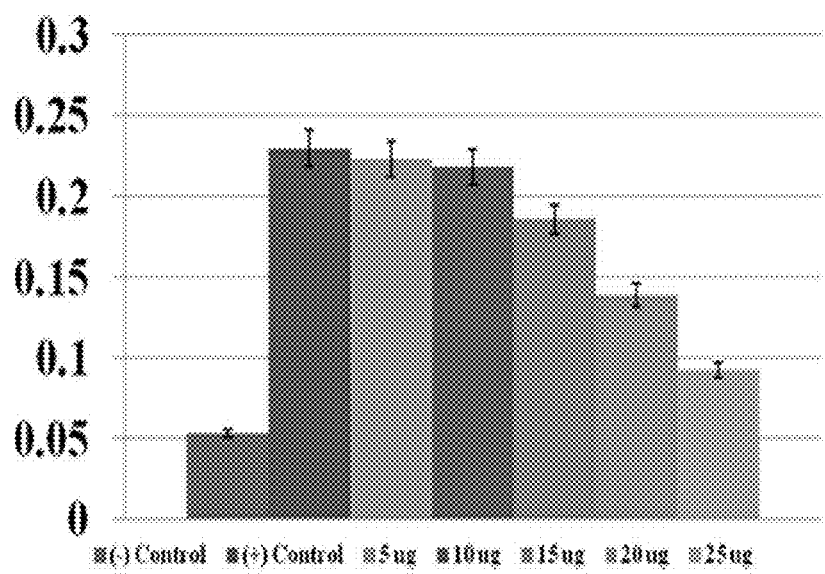
[Fig. 12]

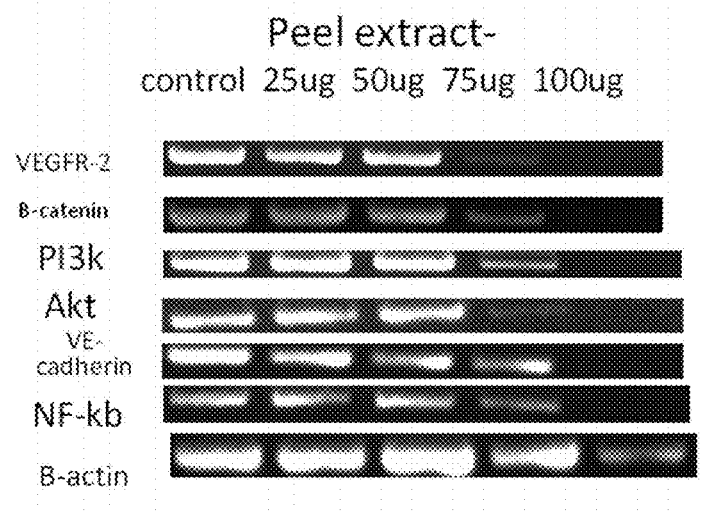

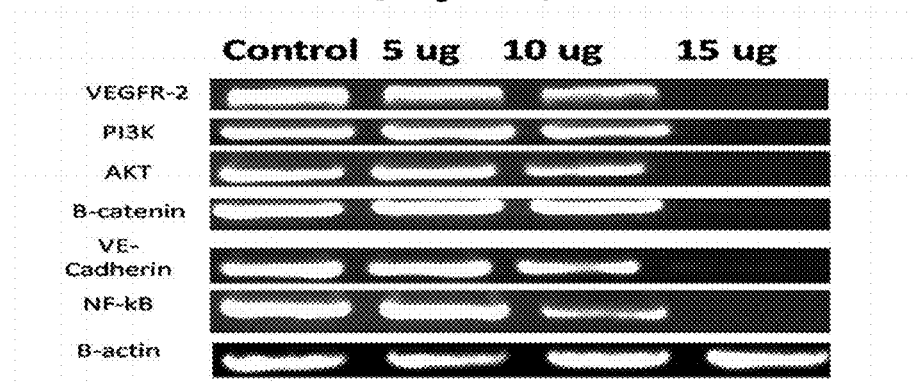
[Fig. 14]

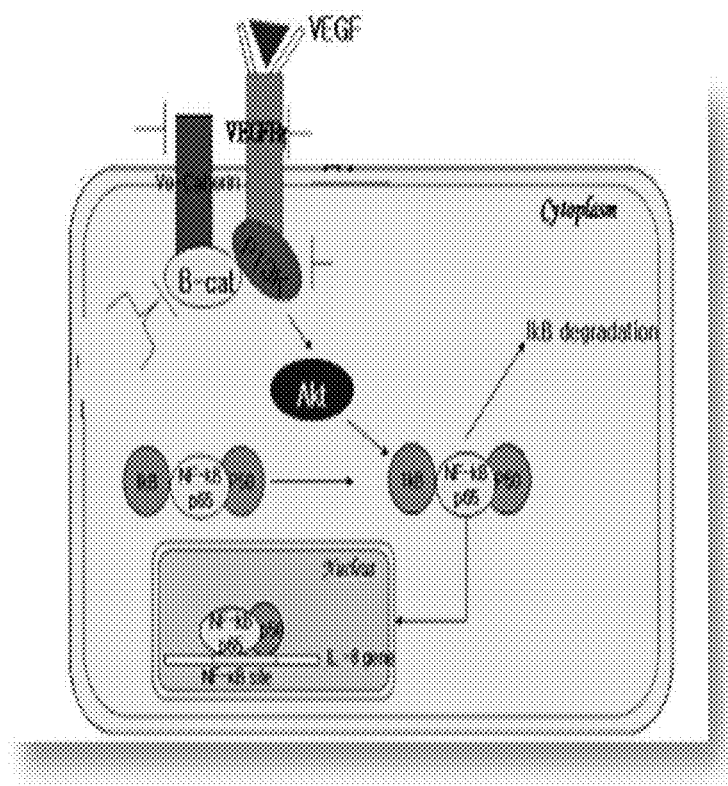
[Fig. 15]

[Fig. 16]
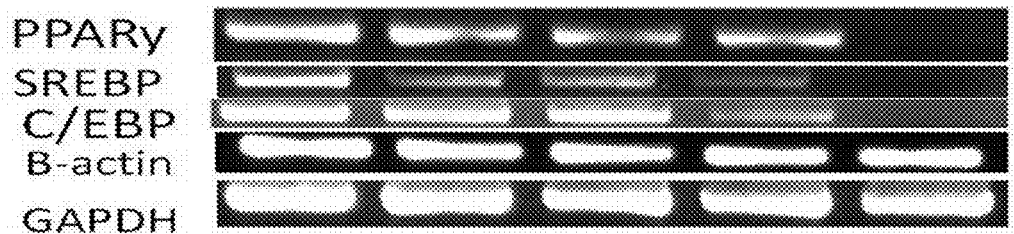
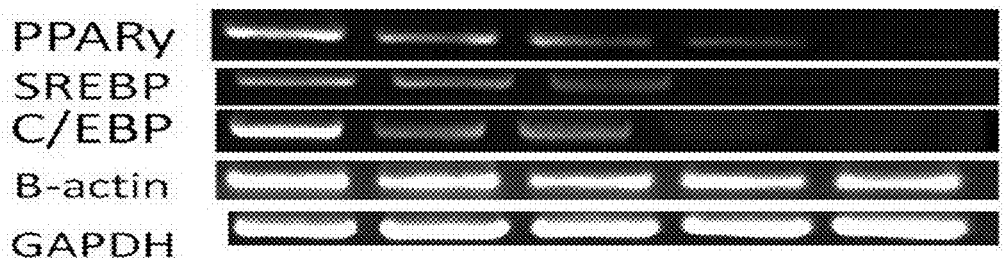

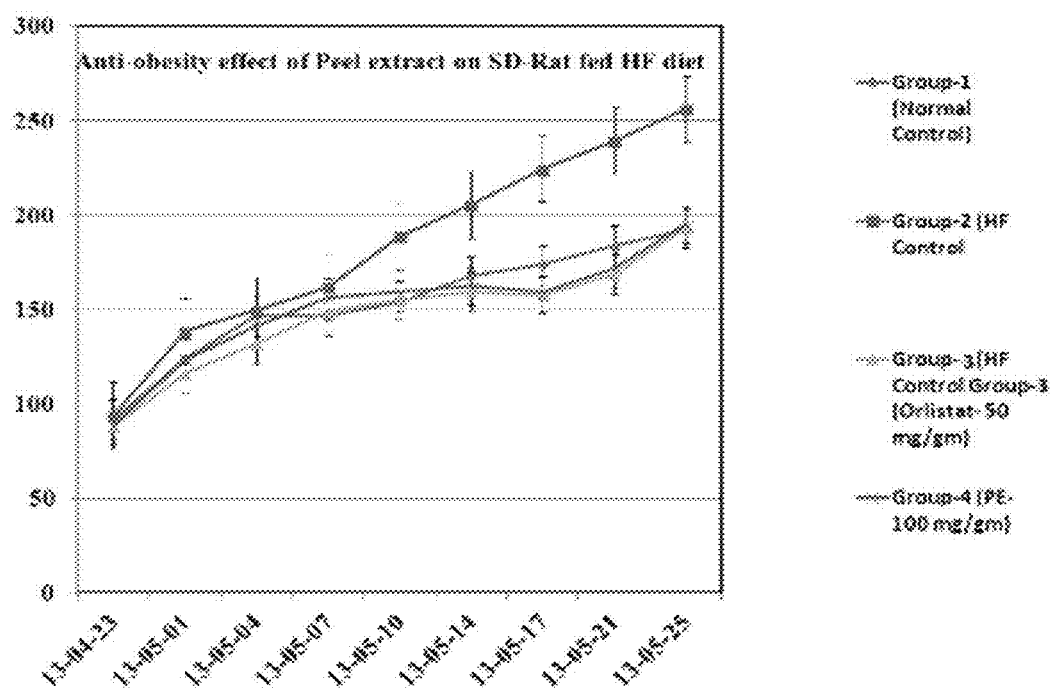
[Fig. 17]

PHARMACEUTICAL COMPOSITION FOR PREVENTING AND TREATING OBESITY, CONTAINING GREEN-TEA SEE HUSK EXTRACT AS ACTIVE INGREDIENT

CROSS REFERENCE TO RELATED APPLICATIONS

This application is a continuation application of International Application No. PCT/KR2014/007401 having an international filing date of Aug. 8, 2014, which claimed the benefit of Korean Application No. 10-2013-0094999 filed Aug. 9, 2013, the entire disclosures of each of which are incorporated herein by reference.

REFERENCE TO SEQUENCE LISTING

This application contains a Sequence Listing submitted as an electronic text file named "Sequence_Listing_TXT.txt", having a size in bytes of 5 KB, and created on Aug. 9, 2013. The information contained in this electronic file is hereby incorporated by reference in its entirety pursuant to 37 CFR § 1.52(e)(5).

BACKGROUND OF THE INVENTION

1. Field of the Invention

The present invention relates to a pharmaceutical composition and a health food for preventing and treating obesity which comprises the green tea (*Camellia sinensis* L.) seed husk extract as an active ingredient.

2. Description of the Related Art

The population of obesity patients increases steadily over the world. The population of domestic obesity patients in Korea reaches 32.7%. In USA, approximately 65% of adults are overweight as of 2000. According to the WHO report, the number of obesity people will be increased by 50% in the next 10 years.

Obesity is the disease characterized by the excessive accumulation of body fat resulted from excess energy caused by the imbalance between energy intake and energy consumption. In general, obesity indicates the condition of excessive body fat. When this obesity continues, various metabolic diseases and adult diseases can be caused, which are exemplified by diabetes, hyperlipidemia, heart disease, stroke, arteriosclerosis, and fatty liver. Recently, the number of obesity people increases rapidly not only in Korea but also in Western advanced countries because of the excessive caloric intake and the lack of exercise, which has been a serious social issue.

The excessive energy supply increases the size and the number of fat cell, and this fat cell is accumulated as body fat, resulting in the obesity. Besides, many different factors including a genetic factor, an environmental factor including westernized diet, a psychological factor, and the energy metabolic disorder, etc, are also known as potential causes of obesity.

Multilateral research efforts have been made world-widely in order to develop anti-obesity agents. Anti-obesity agents are largely divided, according to the mechanism, into such groups as the fat absorption inhibitor, the lipolysis and heat generation promoter, the appetite and satiety regulator, protein metabolism inhibitor, and the food associated emotion controller. The most representative anti-obesity agent is Xenical™ made of oristat which is functioning to inhibit fat absorption and Reductil™ made of sibutramine which is functioning to inhibit appetite by stimulating the sympathetic nervous system. However, according to the previous reports, Xenical™ has such side effects as steatorrhea, abdominal pain, vomiting, pruritus, and liver damage, and Reductil™ has such side effects not only as headache, anorexia, insomnia, and constipation but also as serious cardiovascular diseases, which causes a debate to limit their uses and make the standard of use more strict. In addition to the drug therapy using such anti-obesity agents, other methods such as diet therapy, exercise therapy aiming at increasing energy consumption, psycho therapy, behavior therapy, and surgical treatment have been tried to prevent and treat obesity.

The co-treatment of the method to promote energy consumption and the administration of anti-obesity agents with relatively less side effects is regarded as the safest and most efficient method to treat obesity. However, there is still a doubt in safety of those drugs because of side effects, like Xenical™ and Reductil™.

Angiogenesis is known to be accelerated by at least 20 vasculogenesis factors. Among them, vascular endothelial growth factor (VEGF) is secreted in many kinds of tumor cells and mast cells, which is also known as the most powerful vasculogenesis factor. VEGF is also known as vascular permeability factor. It binds to its receptors, VEGFR-1 (Flt-1) and VEGFR-2 (Flk-1/KDR) to induce the proliferation of endothelial cells and to increase vascular permeability, by which it is involved in the growth and migration of tumor cells and mast cells (Leung, D. W., G. Cachianes, W. J. Kuang, D. V. Goeddel and N. Ferrara (1989) Vascular endothelial growth factor is a secreted angiogenic mitogen. Science 246:1306-1309; Ferrara, N, T. Davis-Smyth (1997) The biology of vascular endothelial growth factor. Endocr. Rev. 18:4-25; Liping Liu, Mohsen Meydani (2003), Angiogenesis Inhibitors May Regulate Adiposity, Nutrition Review, 61(11), 384-387; Jaap G. Neels, Terri Thinnes, and David J. Loskutoff (2004), Angiogenesis in an in vivo model of adipose tissue development, The FASEB Journal express article 10.1096/fj.03-1101fje-.Published online Apr. 14, 2004; G. J. Hausman and R. L. Tichardson (2004), Adipose tissue angiogenesis, J. anim. Sci, 82, 925-934).

Therefore, it is required to develop a natural substance and material which is 100% safe and at the same time displays an excellent anti-obesity effect.

So, the present inventors tried to develop a natural substance with anti-obesity activity. As a result, the inventors confirmed that the green tea (*Camellia sinensis* L.) seed husk extract displayed a significant angiogenesis inhibiting effect and was efficient in reducing fat cells and body weight, and thus the green tea seed husk extract could be efficiently used for a composition for preventing and treating obesity, leading to the completion of this invention.

SUMMARY OF THE INVENTION

It is an object of the present invention to provide a pharmaceutical composition for preventing and treating obesity which comprises the green tea (*Camellia sinensis* L.) seed husk extract or the fraction thereof as an active ingredient.

It is another object of the present invention to provide a health food for preventing and improving obesity which comprises the green tea seed husk extract or the fraction thereof as an active ingredient.

It is also an object of the present invention to provide a pharmaceutical composition for inhibiting angiogenesis which comprises the green tea seed husk extract or the fraction thereof as an active ingredient.

It is further an object of the present invention to provide a method for treating obesity which comprises the step of administering an effective dose of the green tea seed husk extract or the fraction thereof to a subject having obesity.

It is also an object of the present invention to provide a method for preventing obesity which comprises the step of administering an effective dose of the green tea seed husk extract or the fraction thereof to a subject.

It is also an object of the present invention to provide a use of the green tea seed husk extract or the fraction thereof for the preparation of a pharmaceutical composition for preventing and treating obesity.

It is also an object of the present invention to provide a use of the green tea seed husk extract or the fraction thereof for the preparation of a health food for preventing and improving obesity.

It is also an object of the present invention to provide a method for inhibiting angiogenesis which comprises the step of administering an effective dose of the green tea seed husk extract or the fraction thereof to a subject.

It is also an object of the present invention to provide a use of the green tea seed husk extract or the fraction thereof for the preparation of a pharmaceutical composition for inhibiting angiogenesis.

It is also an object of the present invention to provide a use of the green tea seed husk extract or the fraction thereof for the preparation of a health food for inhibiting and improving angiogenesis.

To achieve the above objects, the present invention provides a pharmaceutical composition for preventing and treating obesity comprising the green tea (*Camellia sinensis* L.) seed husk extract or the fraction thereof as an active ingredient.

The present invention also provides a health food for preventing and improving obesity comprising the green tea seed husk extract or the fraction thereof as an active ingredient.

The present invention further provides a pharmaceutical composition for inhibiting angiogenesis which comprises the green tea seed husk extract or the fraction thereof as an active ingredient.

The present invention also provides a method for treating obesity which comprises the step of administering an effective dose of the green tea seed husk extract or the fraction thereof to a subject having obesity.

The present invention also provides a method for preventing obesity which comprises the step of administering an effective dose of the green tea seed husk extract or the fraction thereof to a subject.

The present invention also provides a use of the green tea seed husk extract or the fraction thereof for the preparation of a pharmaceutical composition for preventing and treating obesity.

The present invention also provides a use of the green tea seed husk extract or the fraction thereof for the preparation of a health food for preventing and improving obesity.

The present invention also provides a method for inhibiting angiogenesis which comprises the step of administering an effective dose of the green tea seed husk extract or the fraction thereof to a subject.

The present invention also provides a use of the green tea seed husk extract or the fraction thereof for the preparation of a pharmaceutical composition for inhibiting angiogenesis.

In addition, the present invention provides a use of the green tea seed husk extract or the fraction thereof for the preparation of a health food for inhibiting and improving angiogenesis.

ADVANTAGEOUS EFFECT

The present invention relates to a pharmaceutical composition for preventing and treating obesity which comprises the green tea (*Camellia sinensis* L.) seed husk extract or the fraction thereof as an active ingredient. The green tea seed husk extract of the present invention exhibits the anti-oxidative effect and angiogenesis suppressing effect, suppresses the production of fat cells, and inhibits the expressions of SREBP-1 involved in adipogenesis and PRARr and C/EBPα involved in lipid synthesis, so that it can reduce body weight significantly and has a significant anti-obesity effect. Therefore, the green tea seed husk extract of the invention can be efficiently used as an active ingredient of a pharmaceutical composition for preventing and treating obesity, a health food for preventing and improving obesity, and a pharmaceutical composition for suppressing angiogenesis.

BRIEF DESCRIPTION OF THE DRAWINGS

The application of the preferred embodiments of the present invention is best understood with reference to the accompanying drawings, wherein:

FIG. 1 is a diagram illustrating the method of preparing the green tea (*Camellia sinensis* L.) seed husk extract and the fraction thereof.

FIG. 2 is a diagram illustrating the procedure of crude saponin extraction in the course of tea saponin extraction.

FIG. 3 is a diagram illustrating the procedure of saponin extraction in the course of tea saponin extraction.

FIG. 4 is a diagram illustrating the result of thin layer chromatography with the saponin resulted from tea saponin extraction:
  S: saponin standard;
  A: sonicated group; and
  B: non-sonicated group.

FIG. 5 is a diagram illustrating the cytotoxicity of the green tea (*Camellia sinensis* L.) seed husk extract:
  Peel: green tea seed husk.

FIG. 6 is a diagram illustrating the cytotoxicity of the green tea seed husk originated saponin:
  Peel Saponin: green tea seed husk originated saponin.

FIG. 7 is a diagram illustrating the anti-oxidative effect of the green tea seed husk extract and the saponin originated from the green tea husk extract:
  Peel: green tea seed husk; and
  Peel Saponin: green tea seed husk originated saponin.

FIG. 8 is a diagram illustrating the angiogenesis suppressing effect of the green tea seed husk extract:
  Peel: green tea seed husk.

FIG. 9 is a diagram illustrating the angiogenesis suppressing effect of the saponin originated from the green tea seed husk:
  Peel Saponin: green tea seed husk originated saponin.

FIG. 10 is a diagram illustrating the cell adhesion inhibiting effect of the green tea seed husk extract.

FIG. 11 is a diagram illustrating the fat cell inhibiting effect of the green tea seed husk extract:
  Peel: green tea seed husk.

FIG. 12 is a diagram illustrating the fat cell inhibiting effect of the saponin originated from the green tea seed husk:
  Peel Saponin: green tea seed husk originated saponin.

FIG. 13 is a diagram illustrating the angiogenesis suppression mechanism of the green tea seed husk extract:
Peel: green tea seed husk.

FIG. 14 is a diagram illustrating the angiogenesis suppression mechanism of the saponin originated from the green tea seed husk:
Peel Saponin: green tea seed husk originated saponin.

FIG. 15 is a diagram illustrating the angiogenesis suppression mechanism.

FIG. 16 is a diagram illustrating the obesity inhibiting mechanism of the green tea seed husk extract and the saponin originated from the same:
Peel: green tea seed husk; and
Peel Saponin: green tea seed husk originated saponin.

FIG. 17 is a diagram illustrating the body weight reducing effect of the green tea seed husk extract:
Peel: green tea seed husk;
Group 1: normal diet group;
Group 2: high fat diet group;
Group 3: high fat diet+Orlistat group; and
Group 4: high fat diet+green tea seed husk group.

DESCRIPTION OF THE PREFERRED EMBODIMENTS

Hereinafter, the present invention is described in detail.

The present invention provides a pharmaceutical composition for preventing and treating obesity comprising the green tea (*Camellia sinensis* L.) seed husk extract or the fraction thereof as an active ingredient.

The present invention also provides a method for treating obesity which comprises the step of administering an effective dose of the green tea seed husk extract or the fraction thereof to a subject having obesity.

The present invention also provides a method for preventing obesity which comprises the step of administering an effective dose of the green tea seed husk extract or the fraction thereof to a subject.

The present invention also provides a use of the green tea seed husk extract or the fraction thereof for the preparation of a pharmaceutical composition for preventing and treating obesity.

The green tea seed husk extract above is preferably prepared by the preparation method comprising the following steps, but not always limited thereto:

1) extracting the green tea seed husk after adding an extraction solvent thereto;
2) filtering the extract obtained in step 1); and
3) concentrating the extract filtered in step 2) under reduced pressure and drying thereof.

In the method above, the green tea seed husk of step 1) is preferably separated from the green tea seed that has been cultivated or purchased, but not always limited thereto.

In the method above, the extraction solvent of step 1) is preferably water, $C_1 \sim C_2$ lower alcohol, or a mixture thereof, but not always limited thereto.

In the method above, the lower alcohol of step 1) is preferably ethanol or methanol, but not always limited thereto. The extraction method is preferably enfleurage, hot water extraction, ultrasonification extraction, or reflux extraction, but not always limited thereto.

In the method above, the concentration under reduced pressure in step 3) is preferably performed by using a vacuum concentrator or a vacuum rotary evaporator, but not always limited thereto. The drying in the method above is preferably performed by low pressure drying, vacuum drying, boil drying, spray drying, or freeze drying, but not always limited thereto.

The fraction of the present invention can be obtained by extracting the green tea seed husk with a solvent selected from the group consisting of n-hexane, chloroform, ethyl acetate, and butanol, step-wise or by additional extraction, but not always limited thereto.

The green tea seed husk extract or the fraction thereof preferably displays the anti-obesity activity by suppressing angiogenesis, but not always limited thereto.

In a preferred embodiment of the present invention, the present inventors prepared the green tea seed husk extract and the fraction from the prepared extract (see FIG. 1).

The present inventors also extracted saponin from the green tea seed husk extract above (see FIG. 2 FIG. 4).

To examine cytotoxicity of the green tea seed husk extract, the extract was treated to human umbilical vein endothelial cells (HUVECs), and then optical density was measured with a plate reader. As a result, it was confirmed that the extract did not exhibit cytotoxicity (see FIG. 5).

To investigate cytotoxicity of the saponin originated from the green tea seed husk, the saponin originated from the green tea seed husk was treated to human umbilical vein endothelial cells (HUVECs), and optical density was measured with a plate reader. As a result, it was confirmed that the saponin originated from the green tea seed husk did not have cytotoxicity (see FIG. 6).

To examine the anti-oxidative effect of the green tea seed husk extract, FRAP (ferric reducing ability assay of plasma) was performed via the method of Benzie and Strain. As a result, it was confirmed that the green tea seed husk extract and the saponin originated from the same had as strong anti-oxidative effect as EGCG known to have a very strong anti-oxidative effect (see FIG. 7).

To investigate the angiogenesis suppressing effect of the green tea seed husk extract, the extract was treated to human umbilical vein endothelial cells (HUVECs). As a result, it was confirmed that the green tea seed husk extract suppressed angiogenesis dose-dependently (see FIG. 8).

To investigate the angiogenesis suppressing effect of the saponin originated from the green tea seed husk, the saponin originated from the green tea seed husk was treated to human umbilical vein endothelial cells (HUVECs). As a result, it was confirmed that the saponin originated from the green tea seed husk suppressed angiogenesis dose-dependently (see FIG. 9).

To investigate the effect of the green tea seed husk extract on cell adhesion, the green tea seed husk extract was treated to the human mononuclear cell line U937 (American Type Culture Collection, Rockville, Md.) at different concentrations. 5 random faces of the cell culture plate well were selected and photographed by using a digital camera (Nikon, Coolpix). The number of real cells was counted from the images obtained above by using the NIH image program. Then, the number of adhered cells from all the five faces was counted. As a result, it was confirmed that the green tea seed husk extract was very efficient in inhibiting cell adhesion (see FIG. 10).

To examine the fat cell reducing effect of the green tea seed husk extract, the green tea seed husk extract was treated to 3T3-L1 preadiopocytes at different concentrations, followed by staining with oil-red and the working solution. Then, the stained intracellular lipid was observed under the microscope. As a result, it was confirmed that the green tea seed husk extract reduced fat cells dose-dependently (see FIG. 11).

To examine the fat cell reducing effect of the saponin originated from the green tea seed husk, the saponin isolated from the green tea seed husk was treated to 3T3-L1 preadipocytes at different concentrations, followed by staining with oil-red and the working solution. Then, the stained intracellular lipid was observed under the microscope. As a result, it was confirmed that the saponin originated from the green tea seed husk reduced fat cells dose-dependently (see FIG. 12).

To examine the mechanism of angiogenesis suppression of the green tea seed husk extract, the extract was treated to human umbilical vein endothelial cells (HUVECs), followed by investigation of gene expression via PCR. As a result, it was confirmed that the green tea seed husk extract inhibited the expressions of signaling molecules such as β-catenin, vascular epithelium-cadherin, VEGFR-2, PI3 kinase, and NF-κB, and the down-stream group Akt (protein kinase B) (see FIG. 13).

To examine the mechanism of angiogenesis suppression of the saponin originated from the green tea seed husk, the green tea seed husk originated saponin was treated to human umbilical vein endothelial cells (HUVECs), followed by investigation of gene expression via PCR. As a result, it was confirmed that the green tea seed husk originated saponin inhibited the expressions of signaling molecules such as β-catenin, vascular epithelium-cadherin, VEGFR-2, PI3 Kinase, and NF-κB, and the down-stream group Akt (protein kinase B) (see FIG. 14).

To examine the effect of the green tea seed husk extract and the green tea seed husk originated saponin on the mechanism of adipogenesis and lipogenesis, the green tea seed husk extract and the green tea seed husk originated saponin were treated to 3T3-L1 preadipocytes, followed by investigation of gene expression via PCR. As a result, it was confirmed that the green tea seed husk extract of the invention and the saponin originated from the same inhibited the expression of SREBP-1 involved in adipogenesis and PRARr and C/EBPα involved in lipogenesis (see FIG. 16).

To examine the body weight reducing effect of the green tea seed husk extract, the green tea seed husk extract was administered to Sprague-Dawley (SD) rats (TACONIC, Germany) together with high fat diet. As a result, it was confirmed that the body weight reducing effect was significant, compared with the group treated with high fat diet only (see FIG. 17).

To investigate the body weight reducing effect of the green tea seed husk extract, Sprague-Dawley (SD) rats (TACONIC, Germany) were treated with high fat diet alone, high fat diet together with the green tea seed husk extract (comparative control 1), the green tea seed husk extract prepared from the green tea seed regardless of outer skin or inner skin (comparative control 2), and the green tea seed husk extract via oral administration. From the comparison among those groups, it was confirmed that the group treated with the green tea seed husk extract together with high fat diet exhibited a significant body weight reducing effect, compared with the group treated with high fat diet alone, comparative control 1, and comparative control 2 (see Table 3).

Therefore, the green tea (Camellia sinensis L.) seed husk extract of the present invention can be efficiently used for the composition for preventing and treating obesity since the said extract displays a significant angiogenesis suppressing effect and fat cell and body weight reducing effect.

The present invention further provides a pharmaceutical composition for inhibiting angiogenesis which comprises the green tea seed husk extract or the fraction thereof as an active ingredient.

The present invention also provides a method for inhibiting angiogenesis which comprises the step of administering an effective dose of the green tea seed husk extract or the fraction thereof to a subject.

The present invention also provides a use of the green tea seed husk extract or the fraction thereof for the preparation of a pharmaceutical composition for inhibiting angiogenesis.

The green tea seed husk extract or the fraction thereof can be efficiently used for the composition for inhibiting angiogenesis since the green tea seed husk extract or the fraction thereof displays a significant angiogenesis inhibiting effect.

The composition comprising the green tea seed husk extract of the invention can contain one or more additional active ingredients that display the same or similar functions with the active ingredient above.

The composition of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive in this invention is preferably added to the composition above at the ratio of 0.1~90 weight part, but not always limited thereto.

The composition of the present invention can be administered orally or parenterally and be used in general forms of pharmaceutical formulation. The composition of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing the green tea seed husk extract or the fraction thereof with one or more suitable excipients such as starch, calcium carbonate, sucrose or lactose, gelatin, etc. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The composition of the present invention can be administered orally or parenterally. The parenteral administration includes external application, intraperitoneal injection, intrarectal injection, subcutaneous injection, intravenous injection, intramuscular injection and intrathoracic injection.

The effective dosage of the composition can be determined according to weight, age, gender, health condition, diet, administration frequency, administration method, excretion and severity of a disease.

The composition of the present invention is administered by the pharmaceutically effective dose. The term "pharmaceutically effective dose" herein indicates the amount enough to treat the disease with applicable, reasonable or risky concentration. The dose can be determined by considering many factors such as the type of inflammatory disease, severity of the disease, activity of the drug, sensitivity to the drug, administration frequency and pathway, excretion, term of treatment, co-treatment drug and other factors regarded as relevant in the medicinal field.

Particularly, the effective dose of the compound of the present invention is preferably 0.1 mg~100 mg/kg and more preferably 0.5 mg~10 mg/kg, which can be administered every day or every other day, or 1~3 times a day. However, the effective dose can be increased or decreased according to the administration pathway, severity of obesity, gender, body weight, and age of patient, etc, so that the effective dose above cannot limit the present invention in any aspects.

The present invention also provides a health food for preventing and improving obesity comprising the green tea seed husk extract or the fraction thereof as an active ingredient.

The present invention also provides a use of the green tea seed husk extract or the fraction thereof for the preparation of a health food for preventing and improving obesity.

In addition, the present invention provides a use of the green tea seed husk extract or the fraction thereof for the preparation of a health food for inhibiting and improving angiogenesis.

The green tea seed husk extract or the fraction thereof preferably has the activity of preventing obesity or improving obesity, but not always limited thereto.

The green tea seed husk extract above preferably has the activity of suppressing angiogenesis, but not always limited thereto.

The green tea seed husk extract or the fraction thereof of the present invention can be effectively used for the health food composition for preventing and improving obesity since the green tea (*Camellia sinensis* L.) seed husk extract or the fraction thereof has a significant fat cell and body weight reducing effect.

The food herein is not limited. For example, the green tea seed husk extract or the fraction thereof of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The green tea seed husk extract or the fraction thereof of the present invention can be used as a food additive. In that case, the green tea seed husk extract or the fraction thereof of the present invention can be added as it is or as mixed with other food components according to the conventional method. The mixing ratio of active ingredients can be regulated according to the purpose of use (prevention, or improvement). In general, to produce health food or beverages, the green tea seed husk extract or the fraction thereof of the present invention is added preferably by 0.01~15 weight % and more preferably by 0.1~5 weight %. However, if long term administration is required for regulating health condition, the content can be lower than the above but higher content can be accepted as well since the green tea seed husk extract or the fraction thereof of the present invention has been proved to be very safe.

The composition for health beverages of the present invention can additionally include various flavors or natural carbohydrates, etc, like other beverages in addition to the green tea seed husk extract or the fraction thereof. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, etc.) and synthetic sweetening agents (saccharin, aspartame, etc.) can be included as a sweetening agent. The content of the natural carbohydrate is preferably 0.1~2.0 g and more preferably 0.1~1.0 g in 100 ml of the composition of the invention.

The health functional food of the present invention can be prepared by adding the extract or compound of the invention in the course of the food processing procedure or after the food processing procedure. At this time, a taste and smell corrigent can be added, if necessary.

In addition to the ingredients mentioned above, the green tea seed husk extract or the fraction thereof of the present invention can include a variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The green tea seed husk extract or the fraction thereof of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by approximately 20 weight part per 100 weight part of the green tea seed husk extract or the fraction thereof of the invention.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Green Tea (*Camellia sinensis* L.) Seed Husk Extract

The green tea seed was picked up in Suncheon-si, Jeollanam-do, Korea. The seed husk was separated therefrom and washed thoroughly. The husk was dried by hot-air drying at 50° C. for 3 days, followed by pulverization with 40 mesh. Then, 70% ethanol was added to the green tea seed husk powder, followed by circulation at room temperature. The extract was filtered, concentrated, and freeze-dried. As a result, 25 g of the green tea seed husk extract was prepared.

Example 2: Preparation of Green Tea (*Camellia sinensis* L.) Seed Husk Extract Solvent Fraction 4 g of the green tea seed husk extract obtained in Example 1 was suspended in 50 ml of water. 100% hexane at the equal volume to the above was added thereto, followed by shaking. This procedure was repeated three times. As a result, 363.5 mg of the hexane fraction was obtained. Chloroform at the equal volume was added to the water layer remaining after the elimination of the hexane fraction above, followed by shaking. This procedure was repeated three times. As a result, 195.9 mg of the chloroform fraction was obtained. Ethyl acetate at the equal volume was added to the water layer remaining again and 97.8 mg of the ethyl acetate fraction was obtained by the same manner as described above. Butanol at the same volume was added to the water layer remaining again and as a result 199.9 mg of the butanol fraction was obtained by the same manner as described above. The remaining water layer was concentrated and at last 130.3 mg of the water fraction was obtained (FIG. 1).

Example 3: Extraction of Saponin from the Green Tea (Camellia sinensis L.) Seed Husk Extract <3-1> Preparation of Active 4-Bromophthalic Anhydride To extract saponin from the green tea seed husk extract, 200 g of 4-bromophthalic anhydride was loaded in a 1 L beaker, to which ethanol was added enough to dip 4-bromophthalic anhydride fully, followed by the activation thereof for 2 hours. Then, the mixture was filtered to eliminate ethanol, which continued with washing with ethanol until turbidity became clear. The filtered 4-bromophthalic anhydride was dipped in distilled water, followed by vacuum drying to eliminate ethanol.

<3-2> Extraction of Crude Saponin

The vacuum-filtered 4-bromophthalic anhydride prepared in Example <3-1> was loaded in a 500 ml beaker, to which 200 mL of the green tea seed husk extract obtained in Example 1 was added, followed by reaction at room temperature for 1 hour. Then, the green tea seed husk extract reacting to 4-bromophthalic anhydride was loaded in the column, followed by reaction for 10 hours. To extract crude saponin, 0.3~0.5% NaOH aqueous solution was treated to the column (FIG. 2). At this time, yellow liquid was formed in the column by the reaction of saponin and NaOH. This yellow liquid was the crude saponin fraction.

<3-3> Extraction of Saponin

The crude saponin obtained in Example <3-2> was neutralized in hydrochloric acid aqueous solution (pH 7.0), followed by the reaction of the crude saponin and the activated 4-bromophthalic anhydride via batch reaction. The reaction mixture was loaded in the column, followed by reaction for 10 hours (overnight). Then, the mixture was extracted with 70~95% ethanol aqueous solution. At this time, a white precipitate was formed in the extraction solution, which was the green tea seed husk extract originated saponin (FIG. 3).

<3-4> Confirmation of Green Tea Seed Saponin

To confirm the saponin extracted in Example <3-3> above was the real saponin, thin layer chromatography was performed by using n-butanol:acetic acid:water=4:1:5 as a developing solution. The result was compared with the result obtained from the saponin standard (TEA saponin E1, Vegetable and Tea Science Institute, Japan). As a result, as shown in FIG. 4, the bands of both the sonicated group and the non-sonicated group were detected at the same spot as the saponin standard could be detected, indicating that the extraction of saponin was successful (FIG. 4).

Experimental Example 1: Investigation of Cytotoxicity of the Green Tea (Camellia sinensis L.) Seed Husk Extract Human umbilical vein endothelial cells (HUVECs) were purchased from Young Science (KOREA), and 3~5 generations of the cells were used in this example. The human umbilical vein endothelial cells were cultured in EBM-2 medium (Clonetics, USA) supplemented with hydrocortisone, epidermal growth factor (EGF), basic fibroblast growth factor (bFGF), insulin-like growth factor 1 (IGF-1), vascular endothelial growth factor (VEGF), ascorbic acid, heparin, and 2% FBS (fetal bovine serum) in a 37° C., 5% $CO_2$ incubator. Then, the cells were further cultured in the flasks and plates coated with 2% gelatin (Sigma, USA) until confluence. The cultured human umbilical vein endothelial cells (HUVECs) were then distributed in a 96 well plate at the density of $4 \times 10^4$ cells/well, followed by further culture for 24 hours. The cells were treated with the green tea seed husk extract prepared in Example 1 at the different concentrations of 5, 10, 20, 25, 30, 40, 50, 75, 100, 150, and 200 μg and with the saponin originated from the green tea seed husk purified in Example 3 at the different concentrations of 1.0, 2.5, 5, 10, 15, and 25 μg, followed by culture in a 37° C., 5% $CO_2$ incubator for 48 hours. Then, the culture medium was discarded and instead 20 μl of 0.5% MTT solution was added to each well of the plate, followed by culture for another 4 hours. Then, the medium was eliminated. 40 μl of DMSO was added to each well of the plate. Optical density was measured at 540 nm by using a plate reader.

As a result, as shown in FIG. 5 and FIG. 6, it was confirmed that the green tea seed husk extract did not display cytotoxicity at the concentration of 100 μg, and the green tea seed husk originated saponin did not display cytotoxicity at the concentration of 10.0 μg (FIG. 5 and FIG. 6).

Experimental Example 2: Anti-Oxidative Effect of the Green Tea (Camellia sinensis L.) Seed Husk Extract To investigate the anti-oxidative effect of the green tea seen husk extract, FRAP (ferric reducing ability assay of plasma) was performed via the method of Benzie and Strain (Benzie I F F & Strain J J, Analytical Biochemistry, 239, 70-76, 1996).

Particularly, 300 mM acetate buffer (pH 3.6), 10 mM TPTZ (2,4,6-tripyridyl-s-triazine) dissolved in 40 mM hydrochloric acid (HCl), and 20 mM ferric chloride were mixed at the ratio of 10:1:1 (v/v/v), resulting in the preparation of FRAP reagent. Then, the green tea seed husk extract prepared in Example 1 above or the green tea seed husk originated saponin purified in Example 3 was diluted at the concentration of 1 mg~5 mg. 0.15 mL of the diluted solution was mixed with 3 mL of the prepared FRAP reagent, followed by reaction at 37° C. for 5 minutes. Then, optical density was measured at 593 nm. The result was presented as the amount of $FeSO_4$ in 1 mg of the sample (mM FeSO4 eq./mg extract) by considering EGCG (epigallocatechin-3-gallate) known as a strong anti-oxidant material as the standard.

As a result, as shown in FIG. 7, it was confirmed that the green tea seed husk extract and the saponin originated from the green tea seed husk of the present invention had as strong anti-oxidative effect as that of EGCG (FIG. 7).

Experimental Example 3: Angiogenesis Suppressing Effect of the Green Tea (Camellia sinensis L.) Seed Husk Extract To investigate the angiogenesis suppressing effect of the green tea seed husk extract, the human umbilical vein endothelial cells (HUVECs) separated from the well of the plate cultured earlier by using trypsin-EDTA were distributed in a 24 well culture plate at the density of $2.5 \times 10^4$ cells/well. The cells were treated with the green tea seed husk extract prepared in Example 1 above or the green tea seed husk originated saponin purified in Example 3 at different concentrations, followed by culture in a 37° C., 5% $CO_2$ incubator for 4 hours. Once a tube net was formed, 5 random faces were selected and photographed by a digital camera (Coolpix; Nikon, Japan). From the obtained images, the length of the tube was measured by using the NIH image program.

As a result, as shown in FIG. 8 and FIG. 9, it was confirmed that the green tea seed husk extract and the saponin originated from the green tea seed husk of the present invention had a significant dose-dependent angiogenesis suppressing effect (FIG. 8 and FIG. 9).

Experimental Example 4: Cell Adhesion Inhibiting Effect of the Green Tea (*Camellia sinensis* L.) Seed Husk Extract To investigate the cell adhesion inhibiting effect of the green tea seed husk extract, the human mononuclear cell line U937 (American Type Culture Collection, Rockville, Md.) was cultured in RPMI-1640 medium (Life Technologies, Grand Island, N.Y.) supplemented with 2 mM L-glutamine (Life Technologies), 10 mM HEPES, 100 unit/mL of penicillin, 100 µg/mL of streptomycin, and 10% FBS in a 37° C., 5% $CO_2$ incubator. The U937 cells were centrifuged at 100 rpm for 5 minutes, followed by concentration ($10^6$ cells/mL). The concentrated cells were re-distributed in a 24 well plate. The green tea seed husk extract prepared in Example 1 was added or not added thereto, followed by culture for 20 hours. 5 random faces of the cell culture plate well were selected and photographed by using a digital camera (Nikon, Coolpix). The number of real cells was counted from the images obtained above by using the NIH image program. Then, the number of adhered cells from all the five faces was counted.

As a result, as shown in FIG. 10, it was confirmed that the green tea seed husk extract of the present invention had a significant cell adhesion inhibiting effect (FIG. 10).

Experimental Example 5: Fat Cell Reducing Effect of the Green Tea (*Camellia sinensis* L.) Seed Husk Extract To investigate the fat cell reducing effect of the green tea seed husk extract, 3T3-L1 preadipocytes were cultured in DMEM supplemented with 10% FBS until the cells covered the bottom of the culture flask completely. The culture continued for 2 more days. The differentiation of the preadipocytes into fat cells was induced by adding an induction medium (MDI, 0.5 mM 3-isobuty-1-methylxanthine, 0.5 µM dexamethasone, and 10 µg/ml of insulin). 3 days later, the medium was replaced with normal DMEM supplemented with 10% FBS. The medium was replaced every other day. The green tea seed husk extract prepared in Example 1 or the green tea seed husk originated saponin purified in Example 3 was treated thereto for 7~10 days at different concentrations. To analyze the differentiation of fat cells, the cultured cells were fixed in formalin. After eliminating the formalin, the cells were washed with 60% isopropanol and dried until white particles were observed. The cells were stained with oil-red and the working solution. After eliminating the dye, the cells were washed with distilled water 4 times. The dye on the non fat area was washed with 100% isopropanol. Then, the stained intracellular lipid was observed under the microscope.

As a result, as shown in FIG. 11 and FIG. 12, it was confirmed that the green tea seed husk extract and the saponin originated from the green tea seed husk reduced fat cells dose-dependently (FIG. 11 and FIG. 12).

Experimental Example 6: Mechanism of Angiogenesis Suppression by the Green Tea (*Camellia sinensis* L.) Seed Husk Extract To investigate the mechanism of the angiogenesis suppression by the green tea seed husk extract, HUVECs were cultured in EBM-2 medium. To examine the mechanism of adipogenesis and lipogenesis as well, 3T3-L1 cells were also cultured. Total RNA was extracted by using TRI solution. DNA synthesis was performed by using RevertAid Premium First Strand cDNA synthesis Kit, and the gene expression was investigated by PCR. At this time, the primers used for the PCR were as shown in Table 1 and Table 2.

TABLE 1

| Gene | Primer sequence | Gene Bank Accession No. | Size (bp) |
| --- | --- | --- | --- |
| VEGFR-2 (KDR) | F 5'-AGG TTG CGT GTT CTT CGA GT-3' (SEQ. ID. NO: 1) R 5'-CCC AAA GTG CTG GGT TTT TA-3' (SEQ. ID. NO: 2) | M_002253.2 | 934 |
| PI3K (PIK3CA) | F 5'-CGT GTG CCA TTT GTT TTG AC-3' (SEQ. ID. NO: 3) R 5'-TCA AAC CCT GTT TGC GTT TAC-3' (SEQ. ID. NO: 4) | NM_006218.2 | 536 |
| VE-Cadherin (CDH5) | F 5'-GGA AGG AGA CAC CAA GCT CA-3' (SEQ. ID. NO: 5) R 5'-CTT GTC ATG CAC CAG TTT GG-3' (SEQ. ID. NO: 6) | NM_001795.3 | 322 |
| β-Catenin (CTNNB1) | F 5'-GGT GGG CTG GTA TCT CAG AA-3' (SEQ. ID. NO: 7) R 5'-GGC AAC TGG TAA ACT GTC AA-3' (SEQ. ID. NO: 8) | NM_001098209.1 | 629 |
| AKT-1 | F 5'-CCG ATT CAC GTA GGG AAA TG-3' (SEQ. ID. NO: 9) R 5'-AGC GTC GAA AAG GTC AAG TG-3' (SEQ. ID. NO: 10) | NM_005163.2 | 529 |
| NF-kB (RELA) | F 5'-TGG TCA GCT CCC TTC TCT GT-3' (SEQ. ID. NO: 11) R 5'-GCC AGC TTG GCA ACA GAT-3' (SEQ. ID. NO: 12) | NM_001145138.1 | 521 |

TABLE 1-continued

| Gene | Primer sequence | Gene Bank Accession No. | Size (bp) |
|---|---|---|---|
| β-actin (ACTB) | F 5'-CTC CTG AGC GCA AGT ACT CC-3' (SEQ. ID. NO: 13) R 5'-ACA TCT CAA GTT GGG GGA CA-3' (SEQ. ID. NO: 14) | NM_001101.3 | 632 |

TABLE 2

| Gene | Primer sequence | Gene Bank Accession No. | Size (bp) |
|---|---|---|---|
| PRAR-γ | F 5'-CTG GCC TCC CTG ATG AAT AA-3' (SEQ. ID. NO: 15) R 5'-GGG TGA AGG CTC ATG TCT GT-3' (SEQ. ID. NO: 16) | NM_001127330.1 | 393 |
| SREBP-1 | F 5'-TTG CAC CAG AGA GCA TTT TG-3' (SEQ. ID. NO: 17) R 5'-GAA AAT GAG AGG CTG GTT GC-3' (SEQ. ID. NO: 18) | NM_033218.1 | 593 |
| C/EBPα | F-5'-TTA CAA CAG GCC AGG TTT CC-3' (SEQ. ID. NO: 19) R 5'-CCA CAG GGG TGT GTG TAT GA-3' (SEQ. ID. NO: 20) | NM_007678.3 | 629 |
| GAPDH | F-5'-TGATGACATCA AGAAGGTGGTGAAG-3' (SEQ. ID. NO: 21) R-5'-TCCTTGGAGGC CATGTGGGCCAT-3' (SEQ. ID. NO: 22) | AK191558.1 | 988 |

As a result, as shown in FIG. 13 and FIG. 14, it was confirmed that the green tea seed husk extract and the green tea seed husk originated saponin of the present invention inhibited the expressions of signal transduction associated molecules such as β-catenin, vascular epithelium-cadherin, VEGFR-2, PI3 Kinase, and NF-κB, and the down-stream group Akt (protein kinase B). The result indicates that the extract and the saponin of the invention inhibits the signal transduction so as not to transmit the signal into NF-kB (FIG. 15) and as a result it can inhibit angiogenesis by suppressing the activation of NF-kB (FIG. 13 and FIG. 14). As shown in FIG. 16, it was also confirmed that the green tea seed husk extract of the present invention and the saponin originated from the same inhibited the expressions of SREBP-1 involved in adipogenesis and PRARr and C/EBPα involved in lipogenesis (FIG. 16).

Experimental Example 7: Body Weight Reducing Effect

To investigate the body weight reducing effect of the green tea seed husk extract, the high fat diet fed Sprague-Dawley (TACONIC, Germany) rats were orally administered with the green tea seed husk prepared in Example 1 at the dose of 100 mg/kg for 15 days. Then, the changes in the body weight were observed. The control group rats were fed with high fat diet without taking the extract.

As a result, as shown in FIG. 17, it was confirmed that the body weight was significantly reduced in the group treated with the green tea seed husk extract along with high fat diet, compared with the group fed with high fat diet alone (FIG. 17).

The body weight reducing effect of the green tea seed husk extract was compared with that of the green tea seed extract.

Particularly, the green tea seed was purchased from Yeosu Agricultural Research Institute. Outer skin and inner skin were removed, followed by pulverization. Then, the green tea seed extract (Comparative Example 1) was prepared by the same manner as described in Example 1. Another extract was prepared from the green tea seed without removing outer skin and inner skin (Comparative Example 2).

Then, the body weight reducing effect was observed by the same manner as described in Experimental Example 7.

As a result, as shown in Table 3, it was confirmed that the group treated with the green tea seed husk extract displayed a body weight reducing effect as significant as 50% by that of the groups treated with the green tea seed extracts (Comparative Example 1 and Comparative Example 2) (Table 3).

TABLE 3

| | Green tea seed husk extract + high fat diet | Comparative Example 1 + high fat diet | Comparative Example 2 + high fat diet | High fat diet alone |
|---|---|---|---|---|
| 0 day | 89 g | 89 g | 89 g | 89 g |
| 5 day | 118 g | 139 g | 139 g | 140 g |
| 10 day | 132 g | 164 g | 165 g | 181 g |
| 15 day | 141 g | 189 g | 190 g | 212 g |
| 20 day | 156 g | 211 g | 215 g | 236 g |
| 25 day | 164 g | 228 g | 230 g | 262 g |
| 30 day | 180 g | 239 g | 241 g | 296 g |

INDUSTRIAL APPLICABILITY

As explained hereinbefore, the present invention relates to a pharmaceutical composition for preventing and treating obesity which comprises the green tea (*Camellia sinensis* L.) seed husk extract or the fraction thereof as an active ingredient. The green tea seed husk extract of the present invention exhibits the anti-oxidative effect and the angiogenesis suppressing effect, suppresses the production of fat cells, and inhibits the expressions of SREBP-1 involved in adipogenesis and PRARr and C/EBPα involved in lipid synthesis, so that it can reduce body weight significantly and has a significant anti-obesity effect. Therefore, the green tea seed husk extract of the invention can be efficiently used as an active ingredient of a pharmaceutical composition for preventing and treating obesity, a health food for preventing and improving obesity, and a pharmaceutical composition for suppressing angiogenesis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating obesity comprising the step of administering an effective dose of a green tea (*Camellia sinensis* L.) seed husk extract which is obtained by using water, $C_1$~$C_2$ lower alcohol, or a mixture thereof as a solvent, to a subject having obesity, wherein the husk is dried by hot-air drying before the extraction.

2. The method for preventing or treating obesity according to claim 1, wherein the lower alcohol is ethanol or methanol.

3. The method for preventing or treating obesity according to claim 1, wherein the green tea seed husk extract has the activity of inhibiting angiogenesis.

* * * * *

UNITED STATES PATENT AND TRADEMARK OFFICE
CERTIFICATE OF CORRECTION

| | |
|---|---|
| PATENT NO. | : 9,956,259 B2 |
| APPLICATION NO. | : 15/018004 |
| DATED | : May 1, 2018 |
| INVENTOR(S) | : Jong Deog Kim |

Page 1 of 1

It is certified that error appears in the above-identified patent and that said Letters Patent is hereby corrected as shown below:

On the Title Page

Item (54) and in the Specification, Column 1, Lines 1-4, please delete the title "PHARMACEUTICAL COMPOSITION FOR PREVENTING AND TREATING OBESITY, CONTAINING GREEN-TEA SEE HUSK EXTRACT AS ACTIVE INGREDIENT" and
insert --PHARMACEUTICAL COMPOSITION FOR PREVENTING AND TREATING OBESITY, CONTAINING GREEN-TEA SEED HUSK EXTRACT AS ACTIVE INGREDIENT--

Signed and Sealed this
Sixth Day of November, 2018

Andrei Iancu
*Director of the United States Patent and Trademark Office*

SEQUENCE LISTING

<160> NUMBER OF SEQ ID NOS: 22

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
aggttgcgtg ttcttcgagt                                    20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
cccaaagtgc tgggttttta                                    20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
cgtgtgccat ttgttttgac                                    20

<210> SEQ ID NO 4
<211> LENGTH: 21
<212> TYPE: DNA
<213> ORGANISM: Artificial
<220> FEATURE:
<223> OTHER INFORMATION: PRIMER

<400> SEQUENCE: 4
tcaaaccctg tttgcgttta c                                  21

<210> SEQ ID NO 5
<211> LENGTH: 20
<212> TYPE: DNA
<213> ORGANISM: Artificial
<220> FEATURE:
<223> OTHER INFORMATION: PRIMER

<400> SEQUENCE: 5
ggaaggagac accaagctca                                    20

<210> SEQ ID NO 6
<211> LENGTH: 20
<212> TYPE: DNA
<213> ORGANISM: Artificial
<220> FEATURE:
<223> OTHER INFORMATION: PRIMER

<400> SEQUENCE: 6
cttgtcatgc accagtttgg                                    20

<210> SEQ ID NO 7
<211> LENGTH: 20
<212> TYPE: DNA
<213> ORGANISM: Artificial

-continued

<220> FEATURE:
<223> OTHER INFORMATION: primer

<400> SEQUENCE: 7
ggtgggctgg tatctcagaa                                                   20

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
ggcaactggt aaactgtcca a                                                 21

<210> SEQ ID NO 9
<211> LENGTH: 20
<212> TYPE: DNA
<213> ORGANISM: Artificial
<220> FEATURE:
<223> OTHER INFORMATION: PRIMER

<400> SEQUENCE: 9
ccgattcacg tagggaaatg                                                   20

<210> SEQ ID NO 10
<211> LENGTH: 20
<212> TYPE: DNA
<213> ORGANISM: Artificial
<220> FEATURE:
<223> OTHER INFORMATION: PRIMER

<400> SEQUENCE: 10
agcgtcgaaa aggtcaagtg                                                   20

<210> SEQ ID NO 11
<211> LENGTH: 20
<212> TYPE: DNA
<213> ORGANISM: Artificial
<220> FEATURE:
<223> OTHER INFORMATION: PRIMER

<400> SEQUENCE: 11
tggtcagctc ccttctctgt                                                   20

<210> SEQ ID NO 12
<211> LENGTH: 18
<212> TYPE: DNA
<213> ORGANISM: Artificial
<220> FEATURE:
<223> OTHER INFORMATION: PRIMER

<400> SEQUENCE: 12
gccagcttgg caacagat                                                     18

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
ctcctgagcg caagtactcc                                                   20

```
<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
acatctcaag ttgggggaca                                                   20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ctggcctccc tgatgaataa                                                   20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
gggtgaaggc tcatgtctgt                                                   20

<210> SEQ ID NO 17
<211> LENGTH: 20
<212> TYPE: DNA
<213> ORGANISM: Artificial
<220> FEATURE:
<223> OTHER INFORMATION: PRIMER

<400> SEQUENCE: 17
ttgcaccaga gagcattttg                                                   20

<210> SEQ ID NO 18
<211> LENGTH: 20
<212> TYPE: DNA
<213> ORGANISM: Artificial
<220> FEATURE:
<223> OTHER INFORMATION: PRIMER

<400> SEQUENCE: 18
gaaaatgaga ggctggttgc                                                   20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ttacaacagg ccaggtttcc                                                   20

<210> SEQ ID NO 20
<211> LENGTH: 20
<212> TYPE: DNA
<213> ORGANISM: Artificial
<220> FEATURE:
<223> OTHER INFORMATION: primer
```

```
<400> SEQUENCE: 20
ccacaggggt gtgtgtatga                                             20

<210> SEQ ID NO 21
<211> LENGTH: 25
<212> TYPE: DNA
<213> ORGANISM: Artificial
<220> FEATURE:
<223> OTHER INFORMATION: PRIMER

<400> SEQUENCE: 21
tgatgacatc aagaaggtgg tgaag                                       25

<210> SEQ ID NO 22
<211> LENGTH: 23
<212> TYPE: DNA
<213> ORGANISM: Artificial
<220> FEATURE:
<223> OTHER INFORMATION: PRIMER

<400> SEQUENCE: 22
tccttggagg ccatgtgggc cat                                         23
```